(12) United States Patent
Kim et al.

(10) Patent No.: US 11,382,698 B2
(45) Date of Patent: Jul. 12, 2022

(54) SURGICAL NAVIGATION SYSTEM

(71) Applicants: Kyungpook National University Industry-Academic Cooperation Foundation, Daegu (KR); Korea Advanced Institute of Science and Technology, Daejeon (KR)

(72) Inventors: Jun Young Kim, Daegu (KR); Min Kyu Je, Daegu (KR); Anna Seo, Daegu (KR); Shin Yoon Kim, Daegu (KR); Hyun Deok Kim, Daegu (KR); Hyun Mun Kim, Seoul (KR)

(73) Assignees: Kyungpook National University Industry-Academic Cooperation Foundation, Daegu (KR); Korea Advanced Institute of Science and Technology, Daejeon (KR)

( * ) Notice: Subject to any disclaimer, the term of this patent is extended or adjusted under 35 U.S.C. 154(b) by 524 days.

(21) Appl. No.: 16/345,506

(22) PCT Filed: Oct. 18, 2017

(86) PCT No.: PCT/KR2017/011486
§ 371 (c)(1),
(2) Date: Apr. 26, 2019

(87) PCT Pub. No.: WO2018/080086
PCT Pub. Date: May 3, 2018

(65) Prior Publication Data
US 2019/0274762 A1     Sep. 12, 2019

(30) Foreign Application Priority Data

Oct. 28, 2016 (KR) ........................ 10-2016-0141973

(51) Int. Cl.
*A61B 5/00* (2006.01)
*A61B 34/20* (2016.01)
(Continued)

(52) U.S. Cl.
CPC .............. *A61B 34/20* (2016.02); *A61B 90/00* (2016.02); *A61B 90/361* (2016.02); *A61B 90/39* (2016.02);
(Continued)

(58) Field of Classification Search
CPC . A61B 34/20; A61B 34/2048; A61B 34/2051; A61B 90/00; A61B 90/361; A61B 90/39; A61B 90/37
See application file for complete search history.

(56) References Cited

U.S. PATENT DOCUMENTS 6,205,411 B1   3/2001   DiGioia, III et al.
6,206,929 B1   3/2001   Ochoa et al.
(Continued)

FOREIGN PATENT DOCUMENTS

CN   105208960 A   12/2015
CN   105377175 A   3/2016
(Continued)

*Primary Examiner* — Joel F Brutus
(74) *Attorney, Agent, or Firm* — Downs Rachlin Martin PLLC

(57) ABSTRACT

A surgical navigation system according to one embodiment may comprise: an electromagnetic wave generation unit; a first detection unit attached to a surgical site of an object to detect a position attached to the surgical site; a second detection unit installed in a patient-specific surgical guide instrument inserted into the surgical site to receive the electromagnetic wave and detect the position of the patient-specific surgical guide instrument; a third detection unit installed in the surgical instrument inserted into the surgical site to detect the position of the surgical instrument; an
(Continued)

information processing unit for registering the position of the first detection unit and the position of the third detection unit and for tracking the position of the surgical instrument on the basis of the position of the first detection unit attached to the surgical site, by setting the position of the patient-specific surgical guide instrument as a reference position when the patient-specific surgical guide instrument is inserted into the surgical site; and a display unit for displaying information including the positions of the object and the patient-specific surgical guide instrument and the position of the surgical instrument.

10 Claims, 8 Drawing Sheets

(51) Int. Cl.
*A61B 90/00* (2016.01)
*A61F 2/32* (2006.01)

(52) U.S. Cl.
CPC ................ *A61F 2/32* (2013.01); *A61B 90/37* (2016.02); *A61B 2034/2048* (2016.02); *A61B 2034/2051* (2016.02); *A61B 2034/2055* (2016.02); *A61B 2090/365* (2016.02); *A61B 2090/367* (2016.02); *A61B 2090/3954* (2016.02)

(56) References Cited

U.S. PATENT DOCUMENTS

| | | | |
|---|---|---|---|
| 7,660,623 | B2 | 2/2010 | Hunter et al. |
| 8,974,467 | B2 | 3/2015 | Stone |
| 9,168,153 | B2 | 10/2015 | Bettenga |
| 2004/0152970 | A1 | 8/2004 | Hunter et al. |
| 2005/0021037 | A1* | 1/2005 | McCombs ............. A61B 34/20 606/79 |
| 2005/0203384 | A1* | 9/2005 | Sati ......................... G06F 3/011 600/426 |
| 2008/0033442 | A1 | 2/2008 | Amiot et al. |
| 2012/0232377 | A1 | 9/2012 | Nottmeier |
| 2014/0134586 | A1* | 5/2014 | Stein .................... G09B 23/286 434/262 |

FOREIGN PATENT DOCUMENTS

| | | |
|---|---|---|
| CN | 106170705 A | 11/2016 |
| JP | 2015533310 A | 11/2015 |
| KR | 20160042297 A | 4/2016 |
| KR | 20160097342 A | 8/2016 |
| WO | 2012135190 A2 | 10/2012 |
| WO | 2016160788 A1 | 10/2016 |

\* cited by examiner

FIG. 4
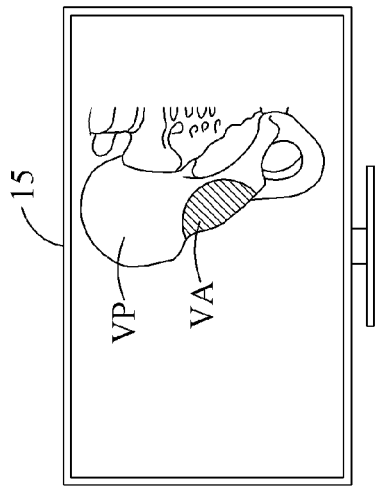
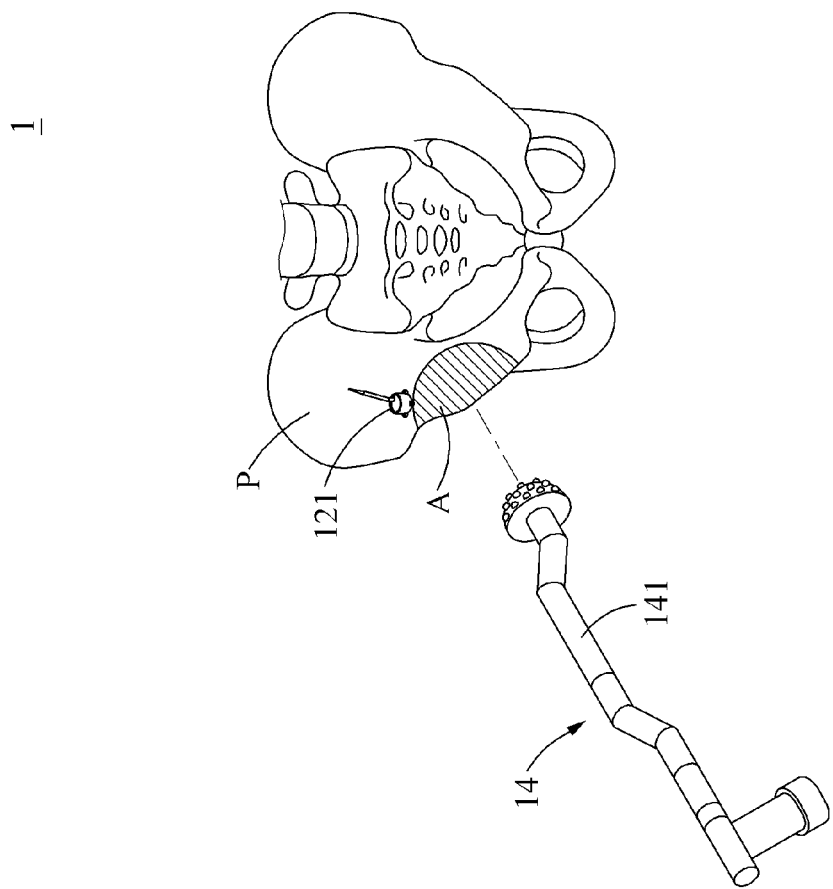

131

SURGICAL NAVIGATION SYSTEM

TECHNICAL FIELD

Example embodiments relate to a surgical navigation system.

BACKGROUND ART

Total hip arthroplasty refers to a surgery conducted to replace, with artificial implants, acetabular fossa and femur, which is a pelvic bone portion forming a hip joint or a pelvic joint. That is, when a hip joint is damaged due to various causes and does not function normally, the arthroplasty may be conducted as a reconstructive surgical procedure using implants to enable the damaged joint to move the same way as a normal hip joint.

A femoral implant used when conducting the arthroplasty includes a globular head, and a stem connected to the head to be inserted into a femoral medullary cavity. In addition, an acetabular implant used to replace a socket-shaped acetabulum includes a metallic cup and a liner in the cup.

When inserting the stem during the arthroplasty, heed may need to be paid to a stem anteversion. The stem anteversion may be desirable at approximately 10 degrees (°) to 20° relative to a condylar axis.

In addition, when inserting the cup during the arthroplasty, heed may need to be paid to a cup inclination and a cup anteversion. The cup inclination may be desirable at approximately 35° to 45° relative to an axial plane, and the cup anteversion may be desirable at approximately 10° to 20° relative to a coronal plane.

For example, U.S. Pat. No. 6,206,929 discloses "bipolar hip prosthesis with locking head."

DISCLOSURE OF INVENTION

Technical Goals

An aspect provides a surgical navigation system to reduce a surgical error that may occur during total hip arthroplasty due to an anatomical difference of individual patients.

An aspect also provides a surgical navigation system that registers and tracks each of a position of a surgical site and a position of a surgical instrument using both an inertial sensor and an electromagnetic sensor.

An aspect also provides a surgical navigation system to reduce a size of a detector portion of the surgical navigation system and a size of a space by using a patient-specific instrument (PSI) including an electromagnetic sensor-based marker.

An aspect also provides a surgical navigation system that tracks a position of a surgical instrument without a distortion of electromagnetic field during a surgical operation by using a PSI including an electromagnetic sensor-based marker only before the surgical operation.

An aspect also provides a surgical navigation system that inserts an acetabular cup and a stem into accurate positions during total hip arthroplasty.

Technical Solutions

According to an example embodiment, there is provided a surgical navigation system including an electromagnetic wave generator, a first detector attached to a surgical site of an object and configured to detect a position attached to the surgical site, a second detector installed in a patient-specific instrument (PSI) which is to be inserted into the surgical site and configured to receive an electromagnetic wave and detect a position of the PSI, a third detector installed in a surgical instrument which is to be inserted into the surgical site and configured to detect a position of the surgical instrument, an information processor configured to register a position of the first detector and a position of the third detector by setting, as a reference position, a position of the PSI being inserted in the surgical site, and to track a position of the surgical instrument based on a position of the first detector being attached to the surgical site, and a display configured to display information including information associated with a position of the object, a position of the PSI, and a position of the surgical instrument.

The information processor may set an insertion path of the surgical instrument along which the surgical instrument is inserted into the surgical site, and the display may further display, on a three-dimensional (3D) object model, the insertion path of the surgical instrument.

The first detector may include an inertial sensor to indicate a position of the surgical site of the object, the second detector may include an electromagnetic sensor to indicate a position of the PSI, and the third detector may include an inertial sensor to indicate a position of the surgical instrument.

The second detector may be removed along with the PSI when the PSI is removed from the surgical site of the object.

The surgical site of the object may include an acetabulum of a pelvis, and the surgical instrument may include a reamer to be inserted into the surgical site. The information processor may set an axis for reaming to be performed by the reamer which is to be inserted into the surgical site of the object.

The surgical site of the object may include a head of a femur and a femoral medullary cavity, and the surgical instrument may include a box chisel, a test femoral stem, and a femoral stem, which are to be inserted into the surgical site. The information processor may set an insertion axis of the box chisel, the test femoral stem, and the femoral stem to be inserted into the object.

When the PSI is inserted in the surgical site of the object, the information processor may match coordinates of the 3D object model and coordinates of the object.

The surgical navigation system may further include a capturer configured to obtain an image of the object in real time, and the display may display the image of the object and an insertion path of the surgical instrument on the image of the object.

Advantageous Effects

According to example embodiments described herein, a surgical navigation system may reduce a surgical error that may occur during total hip arthroplasty due to an anatomical difference of individual patients.

According to example embodiments described herein, a surgical navigation system may register and track each of a position of a surgical site and a position of a surgical instrument by using both an inertial sensor and an electromagnetic sensor.

According to example embodiments described herein, a surgical navigation system may reduce a size of a detector portion of the surgical navigation system and a size of a space by using a patient-specific instrument (PSI) including an electromagnetic sensor-based marker.

According to example embodiments described herein, a surgical navigation system may track a position of a surgical instrument without a distortion of electromagnetic field during a surgical operation by using a PSI including an electromagnetic sensor-based marker only before the surgical operation.

According to example embodiments described herein, a surgical navigation system may insert an acetabular cup and a stem into accurate positions during total hip arthroplasty.

Advantageous effects of the surgical navigation system are not limited to what has been described above, and other effects may be clearly construed by a person having ordinary skill in the art to which the present disclosure pertains from the following description.

BRIEF DESCRIPTION OF DRAWINGS

FIG. 4 is a diagram illustrating a surgical instrument being inserted into a surgical cite along an optimal acetabular axis according to an example embodiment.

BEST MODE FOR CARRYING OUT THE INVENTION

Figure 1:
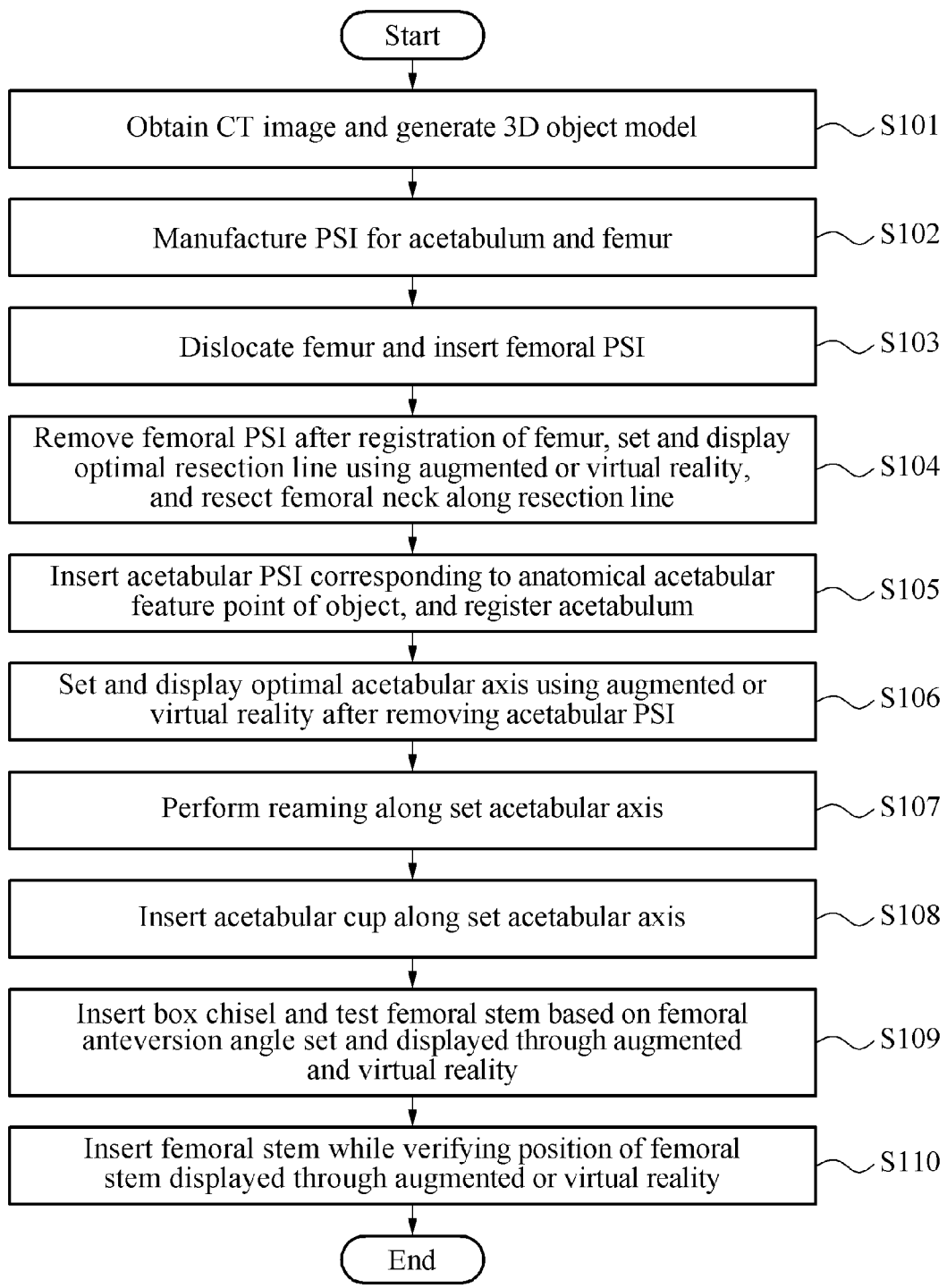
FIG. 1 is a flowchart illustrating a series of steps performed for total hip arthroplasty using a surgical navigation system according to an example embodiment.

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, descriptions of features that are known in the art may be omitted for increased clarity and conciseness.

Terms such as first, second, A, B, (a), (b), and the like may be used herein to describe components. Each of these terminologies is not used to define an essence, order, or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

FIG. 1 is a flowchart illustrating a series of steps performed for total hip arthroplasty using a surgical navigation system according to an example embodiment.

Referring to FIG. 1, in step S101, an operator obtains a computed tomography (CT) image from an object and generates a three-dimensional (3D) object model from the obtained CT image. Herein, the operator may be construed as indicating a human being, a robot, and others conducting or performing a surgical operation. In addition, the object may be construed as indicating a pelvis, a femur, a tibia, and the like of a human being, an animal, and others having or undergoing the surgical operation. For example, a pelvis and a femur are described herein as an example of the object, but the object is not limited to the foregoing example. In addition, the 3D object model may refer to a virtual image obtained by a component such as a processor, for example, a computer, from the CT image, and 3D cloud data. For example, a 3D object image is described herein as an example of the virtual image, but the virtual image is not limited to the foregoing example.

In step S102, the operator manufactures a 3D-shape patient-specific surgical guide instrument in which a sensor, for example, an electromagnetic sensor, is embedded, based on the 3D object model. Here, the patient-specific surgical guide instrument refers to a surgical instrument suitable for a feature point or a characteristic based on an anatomical difference of an individual patient, and is herein also referred to as a patient-specific instrument (PSI). For example, when the object is a pelvis, the operator may manufacture an acetabular PSI of a hemispherical shape corresponding to a shape of an acetabulum. For another example, when the object is a femur, the operator may manufacture a femoral PSI including a concave groove whose shape corresponds to a shape of a head or neck of the femur.

In step S103, the operator dislocates the femur from the pelvis, and inserts the femoral PSI into the head of the femur.

In step S104, the operator performs registration between the femoral PSI and the 3D object model, removes the femoral PSI after the registration, and resects the head of the femur. Here, the registration refers to matching coordinates of an actual model and coordinates of a virtual model, and is also referred to as coordinate registration or geocoding. That is, the registration refers to a processing method that geometrically aligns two or more images to overlap the images. In addition, before removing the femoral PSI and resecting the head of the femur, a surgical navigation system may set and display an optimal resection line using augmented reality or virtual reality.

In step S105, the operator inserts the acetabular PSI into the acetabulum that is suitable for an anatomical feature point of the acetabulum of the object, and performs registration between the acetabular PSI and the 3D object model.

In step S106, after the acetabular PSI is removed by the operator, the surgical navigation system sets an optimal acetabular axis using augmented reality or virtual reality, and displays the set acetabular axis. For example, when the surgical navigation system includes a web camera, the surgical navigation system may capture an image of the pelvis in real time through the web camera, and set an optimal acetabular axis for reaming the acetabulum from the captured image of the pelvis.

In step S107, the operator performs the reaming along the set optimal acetabular axis. The reaming refers to a process of grinding the acetabulum such that a shape of the acetabulum corresponds to a shape of an acetabular cup to be inserted. The operator may use a reamer to perform the reaming.

In step S108, after performing the reaming, the operator inserts the acetabular cup along the set optimal acetabular axis. In step S109, the operator inserts a box chisel and a test femoral stem into the femur based on a femoral anteversion angle that is set and displayed through augmented reality or virtual reality. In step S110, the operator inserts a femoral stem into the femur while verifying a position of the femoral stem being displayed through augmented reality or virtual reality.

Figure 2:
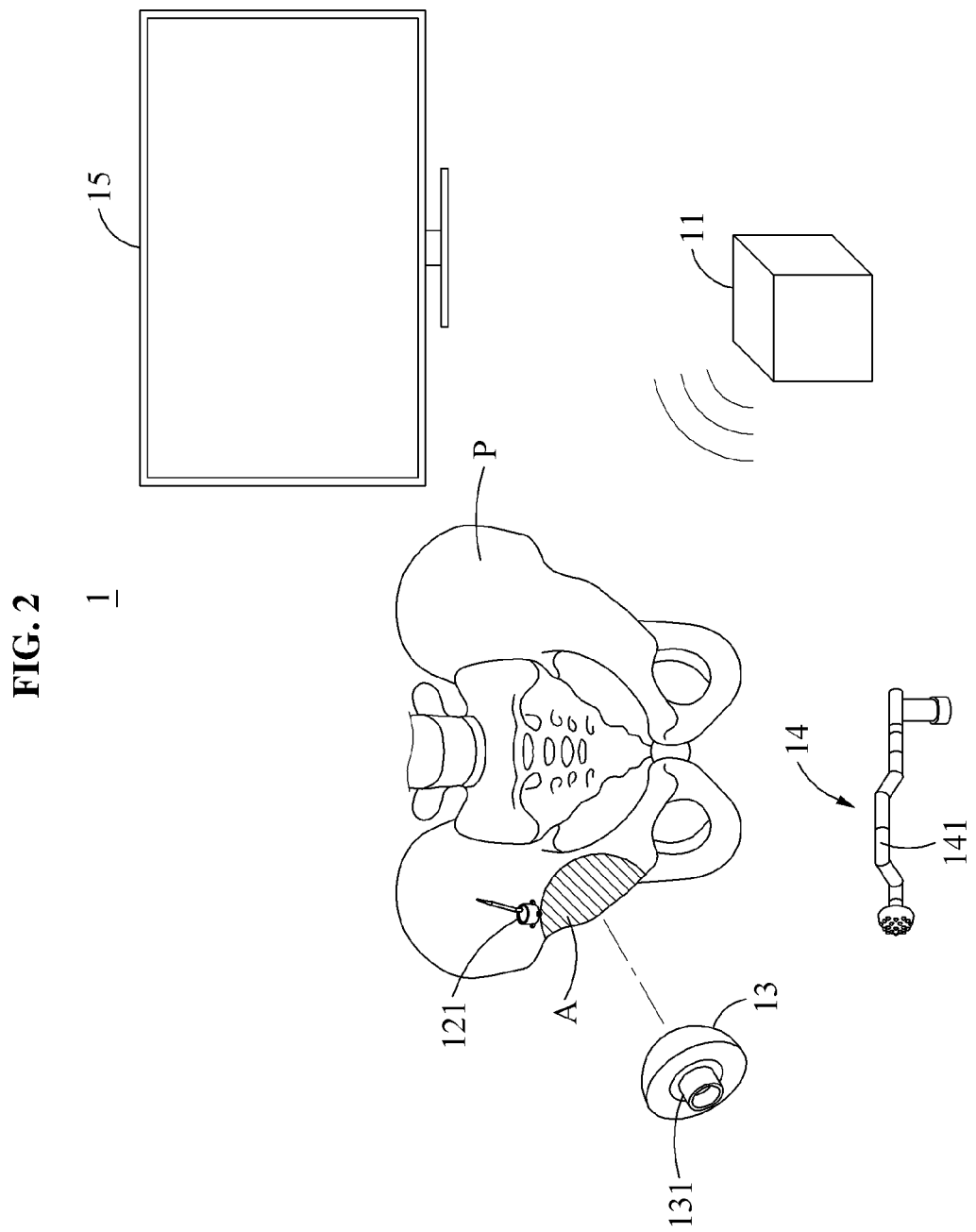
FIG. 2 is a diagram illustrating a procedure performed using a surgical navigation system to insert an acetabular cup according to an example embodiment.
Figure 3:
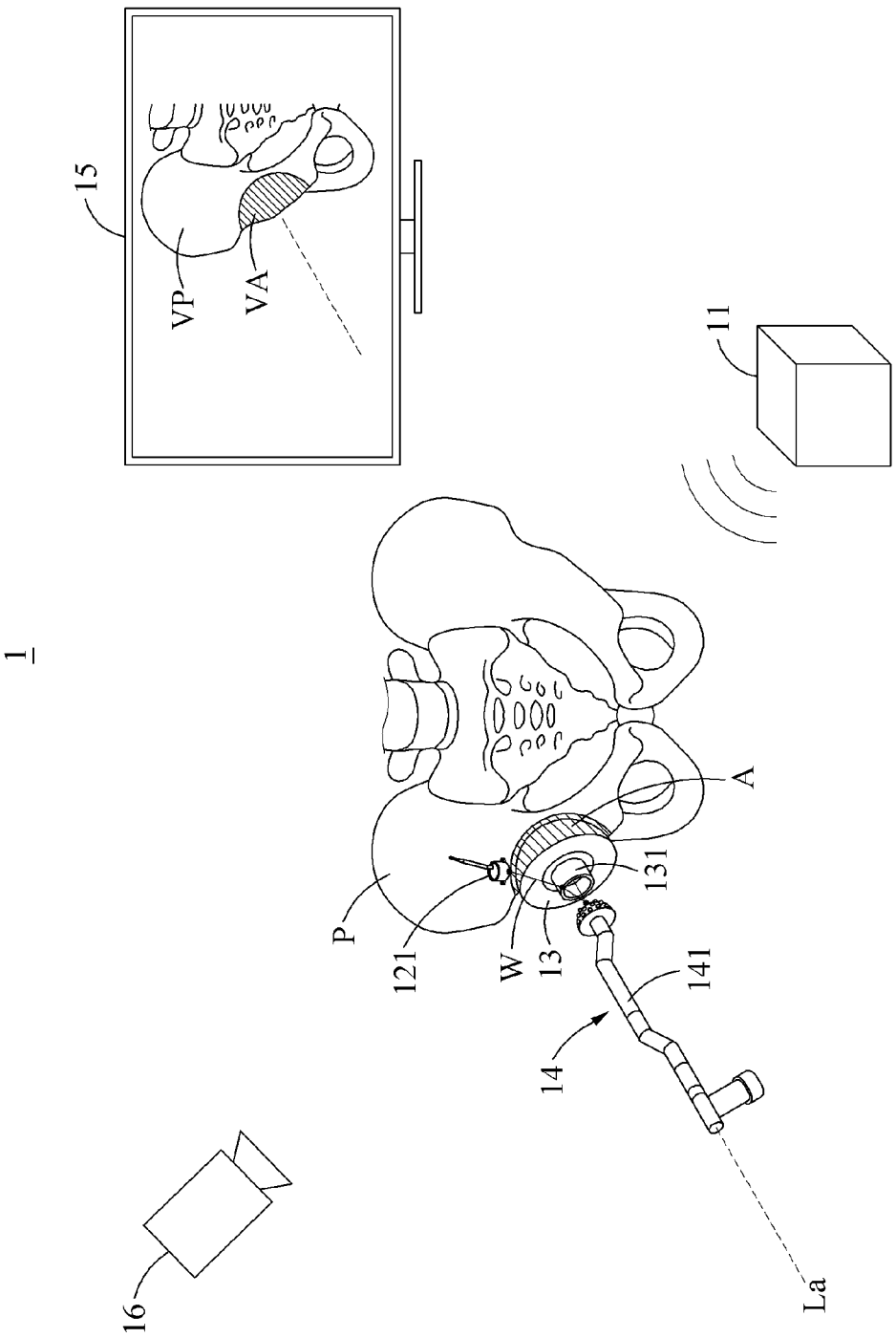
FIG. 3 is a diagram illustrating a patient-specific instrument (PSI) for acetabulum being inserted in a surgical site according to an example embodiment.

FIG. 2 is a diagram illustrating a procedure performed using a surgical navigation system to insert an acetabular cup according to an example embodiment. FIG. 3 is a diagram illustrating an acetabular PSI for acetabulum being inserted in a surgical site according to an example embodiment. FIG. 4 is a diagram illustrating a surgical instrument being inserted into a surgical cite along an optimal acetabular axis according to an example embodiment.

Referring to FIGS. 2 through 4, a surgical navigation system 1 includes an electromagnetic wave generator 11, a first detector 121, a second detector 131, a third detector 141, an information processor (not shown), and a display 15. The surgical navigation system 1 may be used when operating on a hip joint of a human being or an animal. Although the surgical navigation system 1 is provided as an example used for a pelvis and a femur of a human body, examples are not limited to the provided example.

The electromagnetic wave generator 11 may generate an electromagnetic wave. The generated electromagnetic wave may be propagated in a space such as an operating room in which the surgical navigation system 1 is used, and detect a component such as an electromagnetic sensor. That is, by the electromagnetic wave generated from the electromagnetic wave generator 11, positional information of the electromagnetic sensor may be obtained.

The first detector 121 may be attached to a surgical site of an object and detect a position attached to the surgical site. The first detector 121 may include an inertial sensor to indicate a position of the surgical site of the object. The surgical site used herein refers to a target portion on which a surgical operation of total hip arthroplasty is performed. For example, when the object is a pelvis (indicated by P), the surgical site may include an acetabulum (indicated by A) of the pelvis P. In this example, the first detector 121 may be attached to an acetabular margin of the acetabulum A. At a position to which the first detector 121 is attached as described above, it is possible to minimize an amount of surrounding soft tissue being peeled off, and it does not need to resect a portion or site that is irrelevant to the surgical operation, compared to when it is attached to ischium and ilium.

The second detector 131 may receive the electromagnetic wave generated from the electromagnetic wave generator 11, and detect a position of a PSI 13. For example, when the object is the pelvis P, the PSI 13 may be manufactured to correspond to a shape of the surgical site, for example, the acetabulum A, and be inserted into the surgical site A to be engaged with the surgical site A during the surgical operation. The second detector 131 may include an electromagnetic sensor-based marker to indicate a position of the PSI 13. In such a case, when the second detector 131 receives the electromagnetic wave, a position at which the second detector 131 is installed may be detected by the information processor to be described hereinafter. For example, the second detector 131 may be installed in the PSI 13 to be inserted into the surgical site A, and the information processor may obtain positional information of the PSI 13 when the second detector 131 receives the electromagnetic wave. That is, when the PSI 13 is inserted in the surgical site A, the second detector 131 may detect a position in which the PSI 13 is inserted, and then the information processor may obtain positional information of the acetabulum A in which PSI 13 is inserted. Through such a structure described above, the PSI 13 may be temporarily used before the surgical operation is performed to register a position of the surgical site A at which the first detector 121 is arranged, and not be used during the operation. Thus, it may improve an issue of degradation of accuracy of the electromagnetic sensor by a distortion of electromagnetic waves caused by surgical instruments during the operation. For this, the second detector 131 may be removed along with the PSI 13 when it is removed from the surgical site A of the object P.

The third detector 141 may detect a position of a surgical instrument 14. For example, when the object is the pelvis P, the surgical instrument 14 may be a reamer used to ream the acetabulum A, and be inserted into the surgical site A during the surgical operation. The third detector 141 may be installed in the surgical instrument 14 to detect a position of the surgical instrument 14. For example, the third detector 141 may be installed in a handle of the reamer of the surgical instrument 14 as illustrated in FIG. 2. When the third detector 141 detects a position of the surgical instrument 14, the information processor may obtain positional information of the surgical instrument 14. The third detector 141 may include an inertial sensor to indicate a position of the surgical instrument 14. Through such a structure described above, a positional relationship between a position of the surgical site A and a position of the surgical instrument 14 may be obtained as the first detector 121 and the third detector 141 detect the position of the surgical site A and the position of the surgical instrument 14, respectively. That is, relative positional information of the surgical site A and the surgical instrument 14 may be obtained.

The information processor may set, as a reference position, a position of the PSI 13 when the PSI 13 is inserted in the surgical site A, and register a position of the first detector 121 and a position of the third detector 141. FIG. 3 illustrates the PSI 13 being inserted in the surgical site A. The second detector 131 may receive the electromagnetic wave generated from the electromagnetic wave generator 11, and the information processor may obtain positional information of the second detector 131. When the PSI 13 is inserted in the surgical site A, the information processor may set, as the reference position, a position of the second detector 131 when the second detector 131 is positioned at the surgical site A. In such a case, one end of the surgical instrument 14 in which the third detector 141 is installed may be positioned adjacent to the PSI 13, and the information processor may register the position of the first detector 121 and the position of the third detector 141. That is, when the PSI 13 is positioned at the surgical site A, the position of the second detector 131 may be set to be the reference position for the surgical site A. Subsequently, through tracking, the position of the first detector 121 and the position of the third detector 141 may be registered together. The information processor may track a relative position of the surgical instrument 14 by registering, as the reference position, the position of the PSI 13 obtained as described above (the surgical site A in FIG. 3).

The information processor may track a position of the surgical instrument 14 based on a position at which the first detector 121 is attached to the surgical site A. Thus, the information processor may continuously track a position of the surgical instrument 14 while the operation is being performed, by obtaining a relative positional relationship of the surgical instrument 14 in which the third detector 141 is installed based on the position at which the first detector 121 is attached to the surgical site A.

The information processor may set an insertion path (indicated by La) of the surgical instrument 14 towards the surgical site A. While the operation is being performed, an operator may need to accurately insert the surgical instrument 14 into the surgical site A. For this, the information processor may set the insertion path La of the surgical instrument 14 such that the surgical instrument 14 is accurately inserted into the surgical site A, and generate information guiding the operator to insert the surgical instrument 14. For example, when the object is the pelvis P, the information processor may set an axis for the reaming of the surgical instrument 14 to be inserted into the acetabulum A of the pelvis P. In this example, when the operator inserts an acetabular cup into the acetabulum A of the pelvis P after the surgical instrument 14 is used to ream the acetabulum A, the operator may accurately insert the acetabular cup into the acetabulum A without an error.

When the PSI 13 is inserted in the surgical site A of the object P, the information processor may match coordinates of a 3D object model to coordinates of the object. The 3D object model which is generated from a CT image of the object may include 3D coordinates. In such a case, when the information processor registers, as the reference position, the position of the PSI 13 at which the PSI 13 is inserted in the surgical site A, coordinate information of the pelvis P and the acetabulum A may correspond to that of the 3D object model including coordinate information of a virtual pelvis (indicated by VP) and coordinate information of a virtual acetabulum (indicated by VA).

The display 15 may display the insertion path of the surgical instrument 14 on the 3D object model. Through this, the operator may easily verify the insertion path of the surgical instrument 14 while verifying the 3D object model through the display 15, and thus the operation may be performed without an error rather than it is performed depending on a sense of the operator.

The surgical navigation system 1 may further include a lengthwise member W configured to connect the first detector 121, the PSI 13, and the surgical instrument 14. The lengthwise member W may be, for example, a wire, a cable, an arm, a link, and the like. Through such a structure, the PSI 13 may be inserted into the surgical site A along the lengthwise member W and thus be accurately inserted into the surgical site A. In addition, end portions of the lengthwise member W may be connected to preset positions in the first detector 121, the PSI 13, and the surgical instrument 14, and be extended or contracted lengthwise. Through such a structure, consistency may be ensured when registering the position of the first detector 121 and the position of the third detector 141, and thus a difference in the position of the first detector 121 and a difference in the position of the third detector 141, that is an error in relative positional relationship, may be reduced even though an operator using the surgical navigation system 1 changes each time it is used.

The surgical navigation system 1 may further include a capturer 16 configured to capture an object image of the object P in real time. In such a case, the display 15 may display the object image, and an insertion path La of the surgical instrument 14 on the object image. The capturer 16 may be, for example, a web camera, a smartphone camera, and the like, and may obtain an image of the pelvis P in real time and transmit the obtained image to the display 15. The display 15 may also be an indicator. Through such a structure described above, the operator may easily verify a surgical site of an object and an insertion path of a surgical instrument in real time while performing a surgical operation, and thus the operation may be performed without an error, compared to when it is performed depending on a sense of the operator.

Figure 5A:
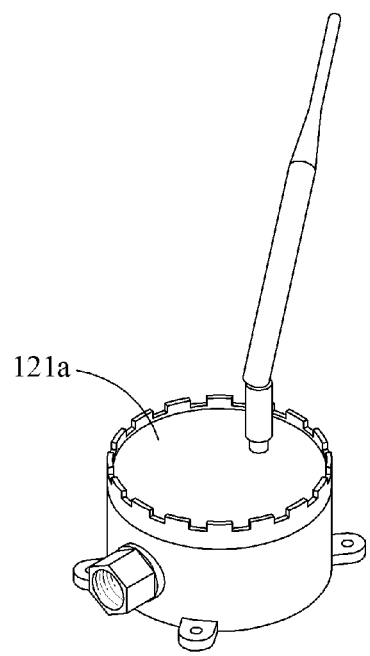
FIG. 5a is a perspective view of an inertial sensor-based marker according to an example embodiment.
Figure 5B:
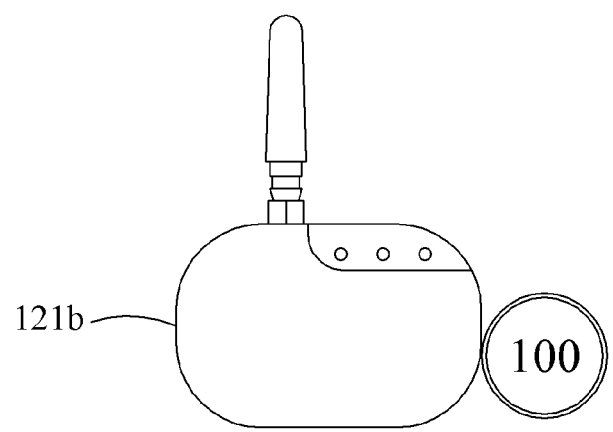
FIG. 5b is a side view of an inertial sensor-based marker according to another example embodiment.
Figure 6:
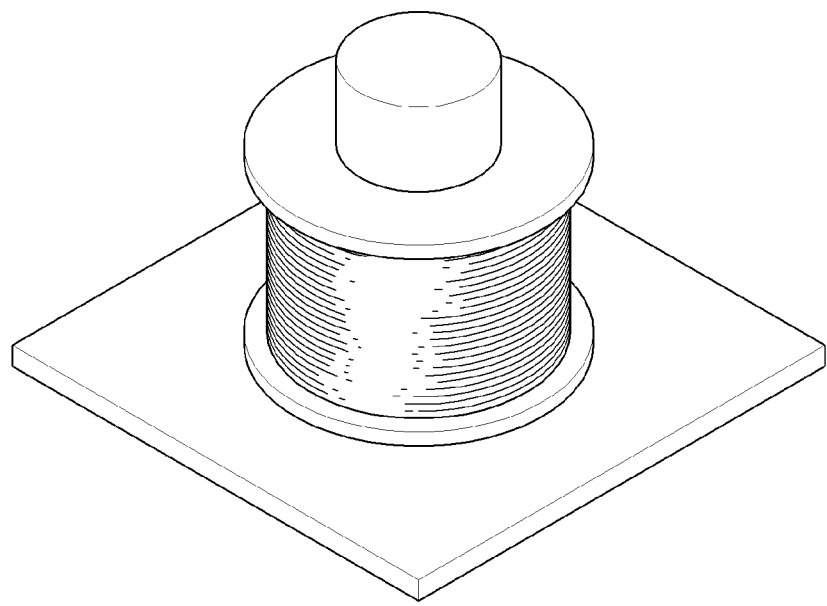
FIG. 6 is a perspective view of an electromagnetic sensor-based marker according to an example embodiment.

FIG. 5a is a perspective view of an inertial sensor-based marker according to an example embodiment. FIG. 5b is a side view of an inertial sensor-based marker according to another example embodiment. FIG. 6 is a perspective view of an electromagnetic sensor-based marker according to an example embodiment.

Referring to FIGS. 5a and 5b, an example of a cylindrical inertial sensor-based marker is illustrated in FIG. 5a, and an example of the first detector 121 and the third detector 141 including a rectangular inertial sensor-based marker of a coin size is illustrated in FIG. 5b. Through such illustrated structures, while a surgical operation is being performed, a side effect such as bleeding may not occur due to a small size of the inertial sensor-based marker, and a path through which a surgical instrument is inserted may not be obstructed.

Referring to FIG. 6, an example of the second detector 131 including a cylindrical electromagnetic sensor-based marker is illustrated. Through such a structure, it may be inserted in and installed at a center of the PSI 13 of a hemispheric shape, and thus it is possible to use a space more effectively while effectively receiving an electromagnetic wave.

Figure 7:
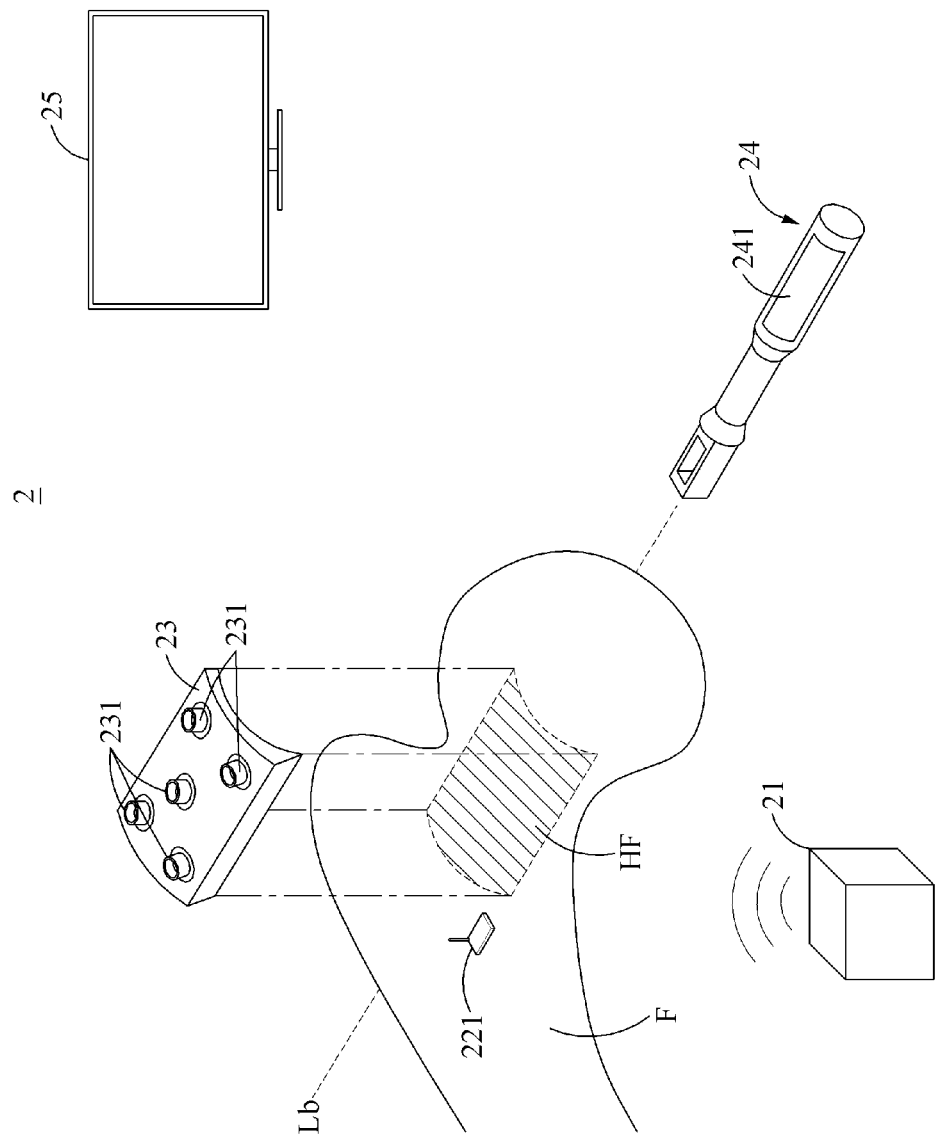
FIG. 7 is a diagram illustrating a procedure performed using a surgical navigation system to insert a femoral stem according to an example embodiment.
Figure 8:
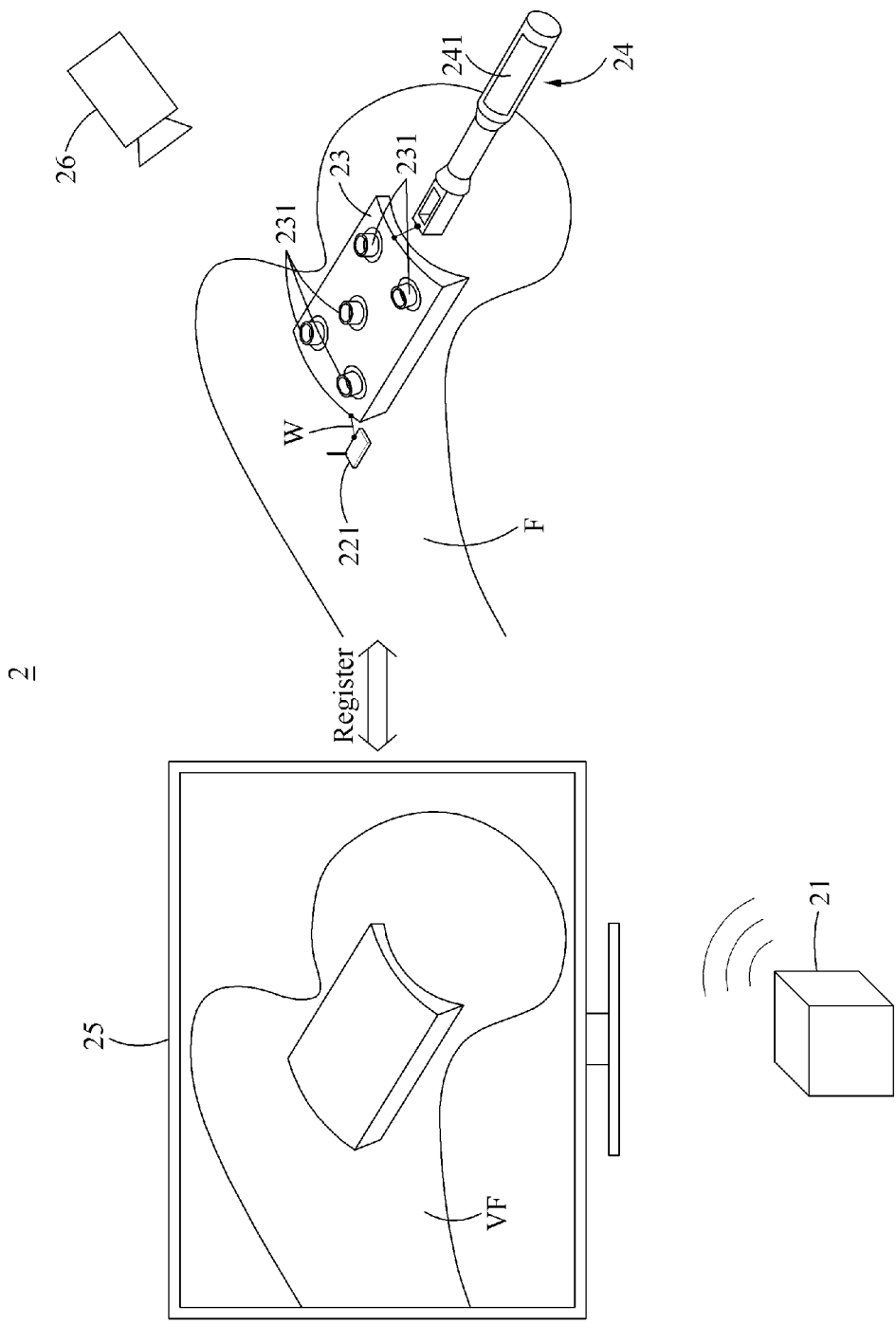
FIG. 8 is a diagram illustrating a PSI for femur being inserted in a surgical site according to an example embodiment.

FIG. 7 is a diagram illustrating a procedure performed using a surgical navigation system to insert a femoral stem according to an example embodiment. FIG. 8 is a diagram illustrating a femoral PSI being inserted in a surgical site according to an example embodiment.

Referring to FIGS. 7 and 8, a surgical navigation system 2 includes an electromagnetic wave generator 21, a first detector 221, a second detector 231, a third detector 241, an information processor, and a display 25.

For example, when an object is a femur (indicated by F), a surgical site may include a head or neck of femur, which is herein referred to as a femoral head (indicated by HF), or a proximal femur. In this example, the first detector 221 may be attached to an edge of the femoral head HF or to the proximal femur.

For example, when the object is the femur F, the second detector 231 may be installed in a PSI 23 manufactured to be suitable to a shape of the femoral head HF.

For example, when the object is the femur F, the third detector 241 may be installed in a surgical instrument 24 to be inserted into the femur F. In this example, the surgical instrument 24 may be a box chisel, a test femoral stem (not shown), and a femoral stem (not shown) to be inserted into the surgical site, for example, the femoral head HF or the proximal femur. Although it is illustrated in FIG. 8 that the box chisel, the test femoral stem, and the femoral stem are inserted into the femoral head HF while there is still the femoral head HF not being resected, examples are not limited thereto. For example, the box chisel, the test femoral stem, and the femoral stem may be temporarily used in a registering process to track a position in relation to the first detector 221 after the femoral head HF or the proximal femur is resected. That is, the box chisel, the test femoral stem, and the femoral stem may be used in the registering process, and also in a tracking process with the femoral head HF being resected.

The information processor may set an insertion axis (indicated by Lb) of the box chisel, the test femoral stem, and the femoral stem to be inserted into the femur F.

The information processor may set, as a reference position, a position of the PSI 23 being inserted in the surgical site HF, and register a position of the first detector 221 and a position of the third detector 241. For example, the information processor may recognize, as coordinates of the PSI 23, the second detector 231 which may be provided as a plurality of second detectors in the PSI 23, and match the recognized coordinates to coordinates on a 3D object model (indicated by VF).

The surgical navigation system 2 may further include a lengthwise member W configured to connect the first detector 221, the PSI 23, and the surgical instrument 24.

The surgical navigation system 2 may further include a capturer 26 configured to obtain an object image of the object F in real time.

According to an example embodiment, a surgical navigation system may reduce a surgical error that may occur in total hip arthroplasty due to an anatomical difference of each individual patient, register and track each of a position of a surgical site and a position of a surgical instrument using both an inertial sensor and an electromagnetic sensor, occupy a smaller space using a detector of a reduced size to increase space efficiency, track a position of a surgical instrument without an electromagnetic distortion during a surgical operation using a PSI including an electromagnetic sensor-based marker only before the surgical operation, and accurately insert an acetabular cup and a stem during the total hip arthroplasty.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A surgical navigation system, comprising:
an electromagnetic wave generator;
a first detector attached to a surgical site of an object at a first position and configured to detect the first position of the surgical site;
a second detector installed in a patient-specific instrument (PSI) which is to be inserted into the surgical site, and configured to receive an electromagnetic wave for detecting a position of the PSI;
a third detector installed in a surgical instrument which is to be inserted into the surgical site and configured to detect a position of the surgical instrument;
an information processor configured to register a position of the first detector and a position of the third detector by setting, as a reference position, a position of the PSI being inserted in the surgical site prior to performing surgery with the surgical instrument, and to track a position of the surgical instrument during a surgical operation after the PSI has been removed from the surgical site based on a position of the first detector attached to the surgical site; and
a display configured to display information including information associated with a position of the object, a position of the PSI, and a position of the surgical instrument.

2. The surgical navigation system of claim 1, wherein the information processor is further configured to set an insertion path of the surgical instrument along which the surgical instrument is inserted into the surgical site, and
the display is further configured to display, on a three-dimensional (3D) object model, the insertion path of the surgical instrument.

3. The surgical navigation system of claim 2, wherein the surgical instrument comprises a reamer to be inserted into the surgical site,
wherein the information processor is configured to set an axis for reaming to be performed by the reamer which is to be inserted into the surgical site of the object.

4. The surgical navigation system of claim 2, wherein the surgical instrument comprises a box chisel, a test femoral stem, and a femoral stem, which are to be inserted into the surgical site,
wherein the information processor is configured to set an insertion axis of the box chisel, the test femoral stem, and the femoral stem to be inserted into the object.

5. The surgical navigation system of claim 1, wherein the first detector comprises an inertial sensor to indicate a position of the surgical site of the object,
the second detector comprises an electromagnetic sensor to indicate a position of the PSI, and
the third detector comprises an inertial sensor to indicate a position of the surgical instrument.

6. The surgical navigation system of claim 5, wherein the second detector is removed along with the PSI when the PSI is removed from the surgical site of the object.

7. The surgical navigation system of claim 1, wherein, when the PSI is inserted in the surgical site of the object, the information processor is configured to match coordinates of a 3D object model and coordinates of the object.

8. The surgical navigation system of claim 1, further comprising:
a capturer configured to obtain an image of the object in real time,
wherein the display is configured to display the image of the object, and an insertion path of the surgical instrument on the image of the object.

9. The surgical navigation system of claim 1, wherein the PSI is a customized instrument manufactured according to a three-dimensional (3D) object model of a patient to have a shape that is complementary to a shape of an anatomical area of the patient.

10. The surgical navigation system of claim 1, wherein the information processor is configured to perform a registration between the reference position of the PSI when it is inserted in the surgical site and a three-dimensional (3D) object model of a patient.

* * * * *